(12) United States Patent
Brennan et al.

(10) Patent No.: US 8,915,904 B2
(45) Date of Patent: Dec. 23, 2014

(54) IMPLANTABLE DEVICE WITH CONFORMING TELEMETRY COIL AND METHODS OF MAKING SAME

(75) Inventors: Jeffrey Brennan, Los Angeles, CA (US); Sean Caffey, Hawthorne, CA (US); Michelle Journey, Carlsbad, CA (US); Fukang Jiang, Pasadena, CA (US)

(73) Assignee: MiniPumps, LLC, Pasadena, CA (US)

( * ) Notice: Subject to any disclaimer, the term of this patent is extended or adjusted under 35 U.S.C. 154(b) by 392 days.

(21) Appl. No.: 13/491,741

(22) Filed: Jun. 8, 2012

(65) Prior Publication Data
US 2012/0316540 A1   Dec. 13, 2012

Related U.S. Application Data

(60) Provisional application No. 61/494,584, filed on Jun. 8, 2011.

(51) Int. Cl.
*A61K 9/22* (2006.01)
*H01Q 1/36* (2006.01)
*A61M 5/142* (2006.01)

(52) U.S. Cl.
CPC .................................... *A61M 5/142* (2013.01)
USPC ..................... 604/891.1; 604/982.1; 604/132; 343/895

(58) Field of Classification Search
CPC ..................... A61M 5/142; A61M 2210/0612; A61N 1/05; A61N 1/37229; A61N 1/0551; A61N 1/3605; A61N 1/37205
See application file for complete search history.

(56) References Cited

U.S. PATENT DOCUMENTS

| | | | |
|---|---|---|---|
| 6,025,725 A | | 2/2000 | Gershenfeld et al. |
| 2007/0191702 A1 | | 8/2007 | Yodfat et al. |
| 2009/0312742 A1* | | 12/2009 | Pang et al. ..................... 604/500 |
| 2012/0277733 A1* | | 11/2012 | Pang et al. ................. 604/892.1 |
| 2012/0323218 A1* | | 12/2012 | Pang et al. ..................... 604/506 |
| 2013/0276974 A1* | | 10/2013 | Pang et al. ..................... 156/300 |

FOREIGN PATENT DOCUMENTS

| | | |
|---|---|---|
| DE | 19840360 A1 | 3/2000 |
| WO | WO-2011/064780 A2 | 6/2011 |

OTHER PUBLICATIONS

International Search Report and Written Opinion issued for International Application No. PCT/US2012/041469, Issued Oct. 24, 2012 and mailed Nov. 2, 2012 (8 pages).

* cited by examiner

*Primary Examiner* — Trinh Dinh
(74) *Attorney, Agent, or Firm* — Bingham McCutchen LLP

(57) ABSTRACT

A spiral-coil antenna conforming to a non-planar contour is deployed, in various embodiments, in an implantable device for controllably ejecting fluid into an anatomic region. The antenna facilitates wireless communications with the implantable device and external charging thereof. In one implementation, the device has a non-planar contour and the spiral coil defines a non-planar surface conforming to the non-planar contour.

13 Claims, 4 Drawing Sheets

IMPLANTABLE DEVICE WITH CONFORMING TELEMETRY COIL AND METHODS OF MAKING SAME

CROSS-REFERENCE TO RELATED APPLICATIONS

This application claims priority to and the benefit of, and incorporates herein by reference in its entirety, U.S. Provisional Patent Application No. 61/494,584, which was filed on Jun. 8, 2011.

FIELD OF THE INVENTION

The technology disclosed herein relates to antennas suitable for integration into implantable devices, as well as to methods of manufacturing such antennas..

BACKGROUND

As patients live longer and are diagnosed with chronic and often debilitating ailments, the result will be an increase in the need to place protein therapeutics, small-molecule drugs, and other medications into targeted areas throughout the body that are currently inaccessible or inconvenient as sites of administration. For example, many vision-threatening diseases, including retinitis pigmentosa, age-related macular degeneration (AMD), diabetic retinopathy, and glaucoma, are incurable and difficult to treat with currently available therapies: oral medications have systemic side effects; topical applications may sting and engender poor compliance; injections require a medical visit, can be painful, and risk infection; and sustained-release implants must typically be removed after their supply is exhausted and, moreover, offer only limited ability to change the dose in response to the clinical situation. Another example is cancer, such as breast cancer or meningiomas, where large doses of highly toxic chemotherapies such as rapamycin or irinotecan (CPT-11) are administered to the patient intravenously, resulting in numerous undesired side effects outside the targeted area.

Implantable drug-delivery systems, which may have a refillable drug reservoir, cannula, and check valve, etc., allow for controlled delivery of pharmaceutical solutions to a specified target. This approach can minimize the surgical incision needed for implantation, and avoids future or repeated invasive surgery or procedures. The implantable drug-delivery systems may, in principle, be turned on and off manually, e.g., by pressing a toggle switch, as used, for example, in pumps used for insulin therapy or intrathecal injections. However, in some applications, the pumps are too small, or too inaccessible after implantation, to allow for manual activation; for example, refillable ocular drug pumps, which usually hold <500 µL, cannot practically be accessed directly post-implantation into the eye, requiring, instead, a remote control to turn the pump on or off. Furthermore, certain drug regimens require complicated drug-delivery protocols, which may change over time depending on patient response. In these circumstances, remote operation of the drug pumps and/or execution of drug delivery protocols can reduce visits to a clinician, the risk of non-compliance, and errors in dosage events caused by self-administration.

Accordingly, various implantable drug-delivery pumps incorporate telemetry capability to facilitate communication with an external monitoring and/or control device. Such implantable pumps may be activated or deactivated remotely; their operating parameters may be non-invasively adjusted; and diagnostic data may be read out from the implantable pumps by the external monitoring device through signals transmitted and received by the telemetry circuitry. During a scheduled visit, a physician may place the monitoring and/or control device near the implantable pump and/or send signals to the implantable pump. The implant, in turn, adjusts the pump parameters and may transmit a response to the monitoring device. Typically, the telemetry circuitry comprises a coil antenna that transmits and receives signals using electromagnetic waves. A number of parameters and effects affecting the efficiency of the coil antenna, e.g., the resonant frequency, gain, quality factor (Q factor), and the thermal effect (Joule effect or heat), typically need to be considered when selecting or designing the coil antenna.

Traditionally, coil antennas incorporated in a medical telemetry systems are hand-wound, utilizing inner and/or outer dimensions as a guide without a set pattern. These coil antennas have variable characteristic parameters and, thus, do not provide optimal efficiency. In addition, the variability among antennas in production—e.g., variations in the resonant frequencies—can create problems when communicating with the external device. For example, the individual implantable devices paired with different telemetry coils may need to be programmed separately to facilitate communication with the external device. Furthermore, loosely wound coil antennas may be difficult to pack on or near the implantable device.

More sophisticated manufacturing methods, such as thin-film or thick-film deposition, etching, or electroplating may also be utilized to form the coil antennas. Antennas generated by these methods, however, are generally planar, whereas the pump devices into which they are embedded often have curved surfaces dictated by the anatomy of the implant site. As a consequence of their inability to conform to the shape of the pump device, these antennas may take up precious "real estate," constraining the overall geometry and/or increasing the footprint of the pump device. Additionally, a coil antenna formed by, for example, film deposition, may be limited in the amount of conductive material utilized, which may not have a good Q factor and, in turn, limits its power transfer.

Consequently, there is a need for an approach to manufacturing, with accuracy, coil antennas that can be easily conformed to various geometries of drug pumps implanted in different anatomical regions.

SUMMARY

In various embodiments, the present invention relates to a coil antenna having a non-planar (e.g., convex or dome-shaped) configuration for conforming to the curvature of a drug-delivery pump implanted in an anatomical region, e.g., the eye. In one embodiment, the coil is a spiral of conductive wire and embedded inside a curved shell to which it conforms; the coil thereby does not impose a geometric constraint on the internal or external configuration of the pump, and may provide greater internal space (e.g., for use as the reservoir of a drug pump) under the coil. In certain embodiments, the coil is configured as a two-dimensional spiral whose nested windings, when they are in close proximity or in contact with each other, form a "pancake" surface (as contrasted, for example, from a typical spring that extends helically in a third dimension), but the surface is non-planar. The coil is two-dimensional in the sense that it does not enclose a three-dimensional space, unlike, for example, a helical coil, whose windings define a cylindrical interior volume. The coil may be disposed against, or embedded in, an outer shell of the pump device.

In some embodiments, the coils are manufactured by cutting a spiral pattern into a sheet of conducting material using, for example, a laser. The generated coils are substantially uniform and can be characterized by precise parameters, which minimizes variance in inductance resulting from variations in coil windings, and increases the reliability of communication with an external controller and the efficiency of communication at the resonant frequency for which the antenna is designed. Additionally, the fabricated coil antennas are typically more compact, easier to integrate into implantable devices, and better able to mechanically stabilize the implantable devices. Further, coils generated by cutting are not subject to the dimensional limitations imposed, for example, by deposition methods, and may, as a result, provide higher power-transfer capability.

Accordingly, in one aspect, the invention pertains to an implantable device (e.g., a drug pump) that is shaped to conform to an anatomic implantation site for controllably ejecting fluid into an anatomic region. The device includes a fluid storage reservoir, a pump mechanism for pumping fluid from the reservoir into the anatomic region, and circuitry for controlling the pump mechanism. The circuitry includes a receiver for receiving wireless communications from an external transmitter and, operatively coupled to the receiver, an antenna having one or more spiral coils, each including multiple nested windings of increasing diameter that are not in lateral electrical contact (e.g., are spaced apart or electrically insulated by a coating surrounding the conducting core of the winding). In some embodiments, the multiple nested windings are concentric; by "concentric" is meant sharing a one or more common central points, or loci, regardless of shape, i.e., the windings need not be circular; instead, the windings and the resulting antenna may have any desired geometric configuration (elliptical, square, rectangular, etc.). Further, changes in radial distances in each winding may be non-uniform. The antenna may be embedded into one or more shells of the implantable device. The device has a non-planar contour (e.g., dome-shaped), and the windings of the spiral coil define a (two-dimensional) non-planar surface conforming to the non-planar contour.

Each winding of the spiral may include a conductive metal coated with a biocompatible insulating material (e.g., parylene), and may be in contact with one or more adjacent windings. The spiral coil windings may be laser-cut from a sheet of metal. In some embodiments, the antenna includes first and second coils each having multiple windings defining a spiral; the spiral of each coil itself defines a two-dimensional, non-planar surface conforming to the non-planar contour. The second coil is aligned with and stacked on top of the first coil; an interior terminus of the first spiral coil winding is electrically connected to that of the second spiral coil winding.

In various embodiments, the control circuitry is configured to wirelessly receive power and/or data via the antenna. For example, the control circuitry can be configured to wirelessly receive data by RF-coupled and/or inductively coupled telemetry.

In a second aspect, the invention relates to a method of manufacturing a spiral-coil antenna conforming to a non-planar contour. In various embodiments, the method includes cutting (e.g., laser-cutting) one or more spiral coils, each having multiple windings of increasing diameter around a central point, from a flat sheet of metal, and permanently conforming the spiral coil(s) to the non-planar contour such that the windings are not in lateral electrical contact and the spiral coil(s) functions as an antenna. Permanently conforming the spiral coil to the non-planar contour may be achieved by, for example, placing the coil into a shell conforming to the non-planar contour; enclosing the spiral coil between two prefabricated shell halves; or conforming the coil to a mold surface conforming to the non-planar contour and applying an adhesive to the coil to retain the mold surface shape. In some embodiments, conforming the coil to a mold surface involves placing the spiral coil into a mold, injecting an adhesive into the mold around the spiral coil, curing the adhesive, and releasing the adhesive material and the spiral coil embedded therein; the cured adhesive may, thus, form a shell around the coil. The term "adhesive," as used herein, broadly refers to any material adhering to the coil, and is not limited to any particular chemical composition. In one implementation, the method includes coating leads of the spiral coil with silicone before injecting the shell material, and then removing the silicone after releasing the cured shell material. In another implementation, the method includes coating the spiral coil with a biocompatible insulating material (e.g., parylene).

The method may further include spacing or insulating the windings from one another such that the windings are not in lateral electrical contact with any other windings, enabling function as an antenna. If the spiral coil has multiple (e.g., two) spiral coils, the method includes aligning and stacking the second spiral coil on top of the first spiral coil and conforming both coils to the non-planar contour. Additionally, the method may include applying an adhesive (e.g., epoxy) to multiple locations between the first and second spiral coils, and electrically connecting an interior terminus of the first spiral coil to that of the second spiral coil using, for example, welding.

As used herein, the term "approximately" or "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
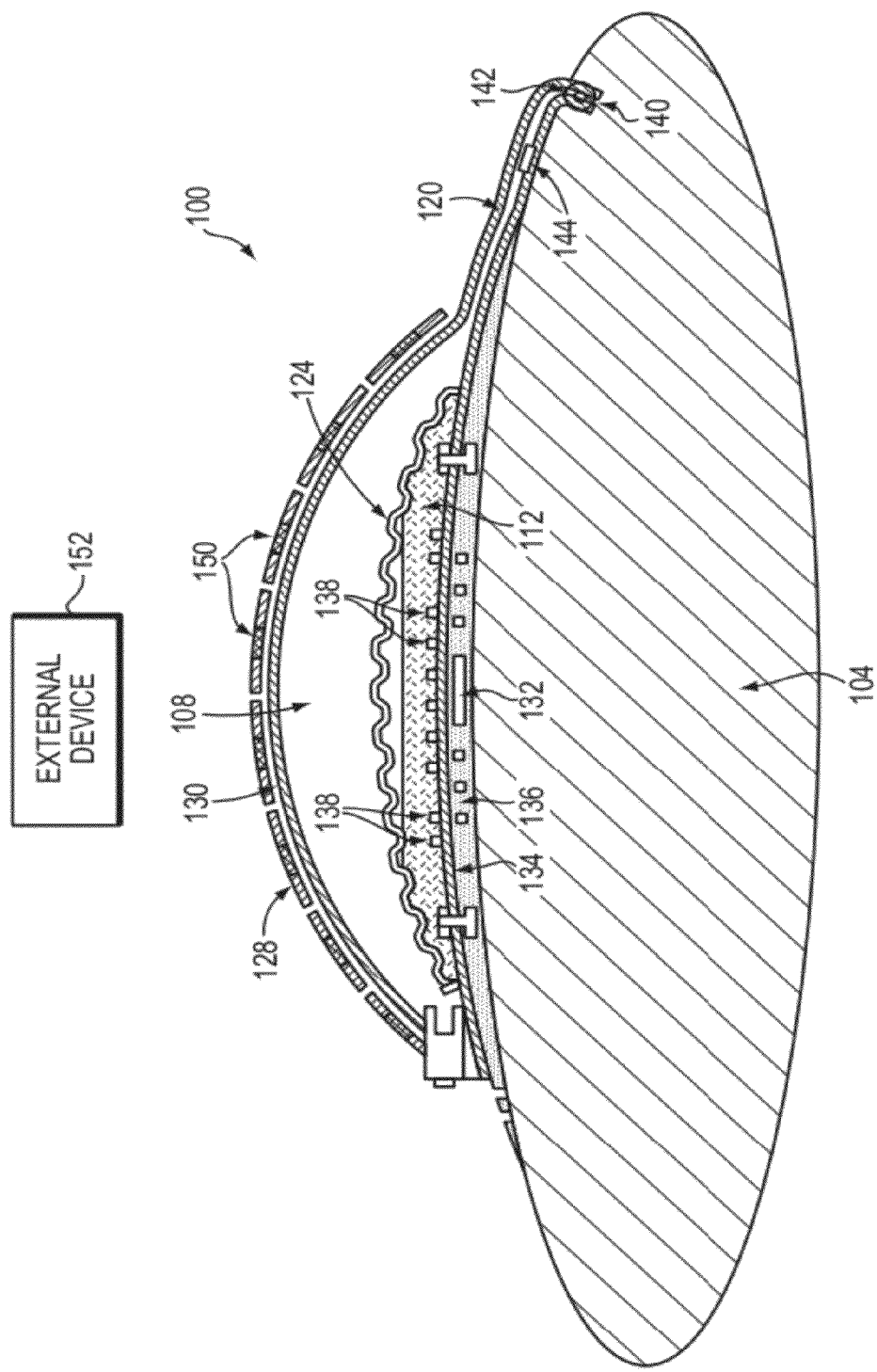
FIG. 1 depicts an exemplary drug-delivery pump in accordance with an embodiment of the invention.

Refer first to FIG. 1, which illustrates an exemplary drug-delivery pump 100 implanted within a patient's eye 104; the details of such pump devices are described, e.g., in U.S. application Ser. No. 12/463,251, filed on May 8, 2009, the entire disclosure of which is hereby incorporated by reference. In the illustrated embodiment, the implantable drug-delivery pump 100 includes a pair of chambers 108, 112 (e.g., formed within parylene envelopes) and a cannula 120. The top chamber 108 defines a drug reservoir that contains one or more drugs to be administered in liquid form, and the bottom chamber 112 contains a fluid (e.g., an electrolytic fluid) which, when subjected to electrolysis, evolves a gas including one or more gaseous products (e.g., in one embodiment, electrolysis of the fluid within the electrolysis chamber produces two gases, $H_2$ and $O_2$). The two chambers 108, 112 are separated by a diaphragm 124. The diaphragm 124 may be elastic and/or corrugated to provide for expansion thereof in response to gas evolution. The diaphragm 124 may be manufactured from one or more parylene films and/or a composite material, for example. The chambers 108, 112 may be positioned within a protective casing or shell 128 that may be made of a relatively rigid biocompatible material (e.g., medical-grade polypropylene, a metal, and/or a biocompatible plastic). The shell 128 may be configured as a domed shape, and provides a hard surface against which an outer wall 130 of the drug reservoir chamber 108 exerts pressure and which protects the pump 100 from external forces. The shell 128 may include a solid, perforated or non-perforated biocompatible material coated in, for example, parylene or epoxy.

Control circuitry 132, including, for example, a battery for power, is embedded under the bottom chamber 112 (e.g., between the bottom wall 134 of the bottom electrolysis chamber 112 and the floor of the pump 100). In one embodiment, the control circuitry 132 is embedded within a protective encapsulation 136 such as, but not limited to, a silicon and/or parylene encapsulation. The control circuitry 132 provides power to one or more electrolysis electrodes 138 positioned within the bottom chamber 112, and may be secured to the electrolysis electrodes 138 by a material such as, but not limited to, a conductive epoxy including a biocompatible conductor material (e.g., gold or silver). The electrolysis electrodes 138 may be formed on or within a parylene film forming the bottom surface of the electrolysis chamber 112. An adhesion layer (e.g., including or consisting of titanium) may be used to adhere the electrolysis electrodes 138 to a bottom surface of the electrolysis chamber 112. Alternatively, the bottom surface of the electrolysis chamber 112 to which the electrolysis electrodes 238 are coupled, or in which they are embedded, may include a substrate formed from a material including, but not limited to, alumina, zirconium oxide, and/or sapphire. Activation of these electrolysis electrodes 138 produces a phase change in the electrolytic fluid within the bottom chamber 112 by causing the fluid to evolve from a liquid to a gaseous state (i.e., generating a gas through electrolysis).

The cannula 120 connects the drug chamber 108 with a treatment site 140. A check valve 142, one or more flow sensors 144, and/or one or more chemical or pressure sensors (not shown) may be positioned within the cannula 120 to control and/or monitor the flow of drug from the drug chamber 108, through the cannula 120, and into the treatment site 140. The check valve 142 may, for example, prevent leakage of a drug from the drug chamber 108 when the electrolysis electrodes 138 are not activated and/or during a refilling process, and/or prevent backward fluid flow through the cannula 120 into the drug chamber 108. Power and/or data telemetry circuitry is included in control circuitry 132 and connected to an antenna 150 (shown as a cross section perpendicular to the plane of the coil windings); the antenna 150 is integrated into the shell 128 to facilitate communication with an external device 152. The telemetry circuitry generally includes a receiver and a transmitter to facilitate wireless communication.

In some embodiments, the antenna 150 includes or consists of one or more coils permitting wireless (e.g., radio-frequency (RF)) communication with the external device 152, which may be a controller (e.g., a portable control handset), and may, further, be used to power the implanted drug pump 100 or charge the battery. The implanted coil can serve as both the transmit and the receive coil. The external controller may be used to send wireless signals to the telemetry circuitry in order to program, re-program, operate, calibrate, or configure the pump 100 before or after implantation. Further, status alerts, dosing schedules, and other relevant information stored by the pump can in its internal memory be downloaded via the coils and verified by the external controller.

Figure 2A:
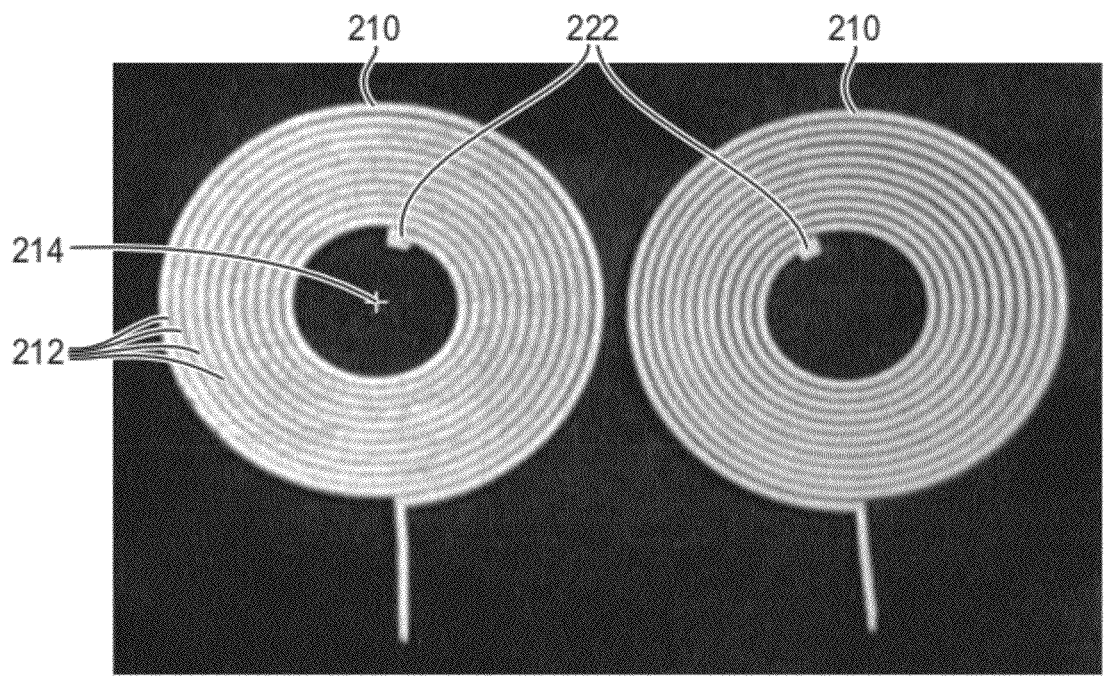
FIG. 2A is a plan view of coils manufactured by a cutting technique in accordance with an embodiment of the invention.

In one embodiment, the coil is formed by winding insulated metal wires. The insulation material that surrounds the metal wires may, for example, consists essentially of expanded TEFLON or epoxy. In another embodiment, the coil is fabricated using an automated cutting technique, as further described below, which generally results in greater accuracy, and facilitates mass-production of coils that have similar high performance (e.g., each coil may have uniform inductance and a similarly high Q factor). Referring to FIG. 2A, the generated individual coils 210 are substantially uniform (e.g., spacings between adjacent coil windings may be substantially constant across the coils), and the two coils have substantially the same diameter and can, generally, be characterized with similar parameters. Additionally, the coils 210 may have a slim profile such that they fit into a limited space of the implantable pump 100. Cutting techniques that may be utilized to fabricate the coils 210 include laser-cutting, stamping, punching, or any technique for generating coils from a metal sheet.

As depicted in FIG. 2A, the coil 210 may have the form of a spiral. The spiral coil 210 includes multiple concentric windings 212 of increasing diameter around a central point 214, each winding being in electrical contact, at its end point(s), with the adjacent winding(s) such that a continuous spiral is formed. Except for the electrical contacts at the end points, the windings are electrically insulated from one another along their entire length. For example, they may be spaced apart (i.e., insulated by air) or insulated by electrically insulating coatings such that they are not in lateral electrical contact with each other. As previously noted, the coil windings may have any desired shape.

In various embodiments, the windings are cut by, e.g., laser-cutting from a sheet of metal that has good conductivity (such as, e.g., gold, copper, etc.). Depending on the material property and dimensions of the windings, lasers with various laser wavelengths, such as a UV lasers, green-light lasers, or infrared lasers, may be used to fabricate the coil 210. The cut metal windings may then be surrounded by a biocompatible insulation material (e.g., parylene). The coil 210 may be embedded into a shell for integration with the implantable pump 100. In some embodiments, the coil 210 is directly embedded into the protective casing 128 of the pump device 100. In alternative embodiments, the coil 210 is embedded into a separate shell that can, thereafter, be attached to the interior surface of the protective casing 128 or of the drug reservoir chamber 108.

Figure 2B:
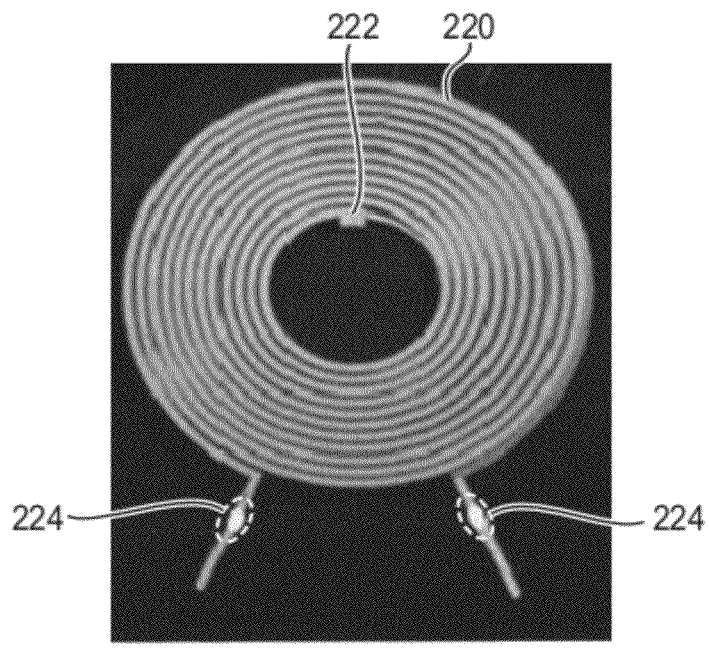
FIG. 2B is a plan view of a coil antenna including two layers of coils in accordance with an embodiment of the invention.

Referring to FIG. 2B, in various embodiments, the coil antenna includes multiple (e.g., two) layers of spiral coils to increase the inductance and thereby the Q factor of the antenna. The multi-layered spiral coil 220 is generated by aligning and stacking the individual coils on top of one another, and then electrically connecting them at their termini. For example, in a double-layer coil, the interior termini 222 of the spiral coils 210 are typically connected. Advantageously, this allows for more convenient positioning of the coil leads 224 through which the coil 220 is coupled to the receiver, transmitter, and/or other circuitry. Whereas an individual coil generally has one lead at the center of the spiral and the other one at the outer terminus, the terminals of a double-layer coil (or, more generally, a coil stack with an even number of layers) may both be placed, adjacent to one another, at the outer termini of the respective coils. In one embodiment, the two layers are separated by insulation (present as a continuous interlayer or at a series of locations) of such that no vertical electrical contact is permitted between the coils 210 (except at the termini 222, as described above).

Figure 3:
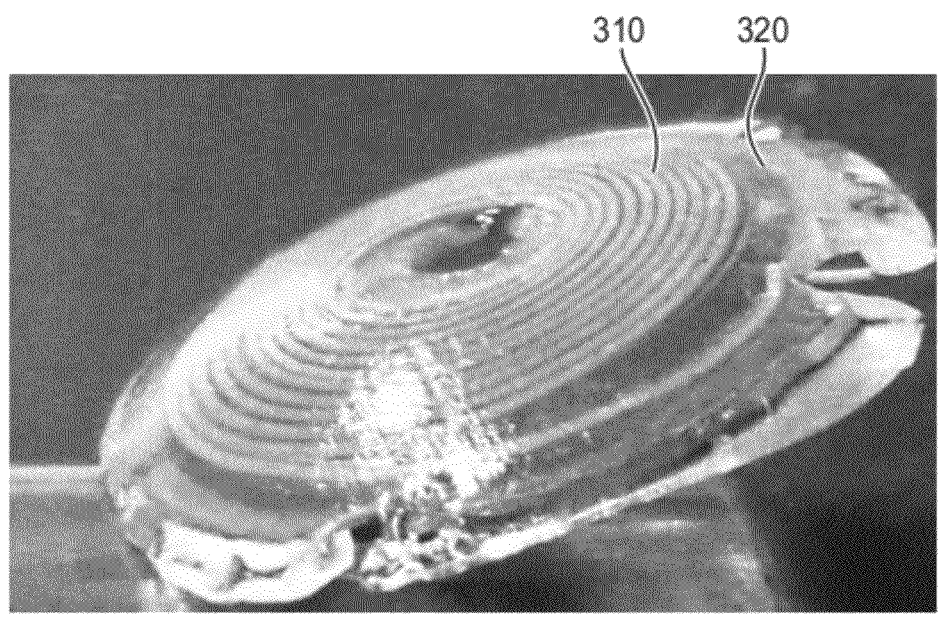
FIG. 3 is a perspective view depicting a coil antenna integrated within a shell conformed to the shape of the drug-delivery pump to provide wireless telemetry and/or recharging in accordance with one embodiment.

The fabricated coil antenna with a single-layer coil 210 or multi-layer coil 220 may be shaped to conform to the geometry of the implantable pump 110. In one embodiment, the spiral coil defines a two-dimensional, non-planar (e.g., dome-shaped) surface that conforms to the non-planar contour of the pump. Referring to FIG. 3, in some embodiments, one or more spiral coils 310 are integrated within an adhesive material forming a shell 320, which may provide or enhance protection of the coil from other components of the implantable pump. The shell 320 may be molded into a shape conforming to a contour of the implantable device. In this way, the coil 310 does not occupy more internal pump space than necessary (providing more space under the coil for, e.g., the drug reservoir), and does not impose constraints on the geometry of the pump, allowing the pump to be conformed to the curvature of the anatomical region, e.g., the eye.

In one embodiment, the coil 310 is "potted" in a material that forms the shell 320 such that the coil 310 is embedded inside the shell 320. The potting material may be transparent or opaque, and may be molded in any unique pattern or shape. In one embodiment, potting involves providing a suitable mold form of the desired shape; applying mold release to the interior surface of the form; placing the coil assembly (i.e., an individual coil or a stack of electrically connected coil layers) into the mold form; closing the form; injecting an adhesive such as, e.g., epoxy, into the form; curing the epoxy in an oven at an appropriate temperature (e.g., 100° C.) or according to epoxy manufacturer guidelines; and opening mold and releasing the molded shell 320 with the embedded coil structure. Alternatively, plastic injection molding may be used to create the shell with an embedded coil. Referring again to FIG. 2B, in various embodiments, during molding, leads 224 of the coil antenna through which the coil 220 is coupled to the receiver, transmitter, and/or other circuitry are protected with a layer of, e.g., silicone, to ensure the conductivity and connectivity of the leads; this protective layer is removed after the shell is released from the mold.

In another embodiment, the coil 310 is conformed to the non-planar surface by enclosing the coil 310 between two prefabricated shell halves. Therefore, coils made from the cutting technique can be advantageously conformed to a two-dimensional, non-planar surface that is difficult to achieve by other methods such as thin/thick film deposition, etching, or electroplating.

In one embodiment, the circuitry associated with the coil converts AC signals transmitted by the external device and received by the coil antenna into a DC voltage, which can power the pump and/or recharge the pump's internal battery. Power transmission is unidirectional and may be accomplished by wirelessly coupling power from an external coil to an internal coil integrated with the pump device packaging. In one embodiment, recharging of the implantable device may be accomplished through utilization of an RF-coupled (near-field or far-field) wireless power link. The frequency of operation can be chosen to suit the application; higher frequencies (e.g., 10 MHz) typically facilitate use of smaller electronic components, and enable greater tissue penetration and higher efficiencies in power coupling, while lower frequencies (e.g., 400 kHz) typically offer lower power consumption and less potential tissue heating due to absorption. In addition, the reader/charger includes a coil or antenna and driver circuitry including a power-amplification stage (e.g., class-C or class-E) specifically designed to couple to resonant circuitry (i.e., a coil and capacitor tuned to the resonant frequency) in the implantable device.

Figure 4:
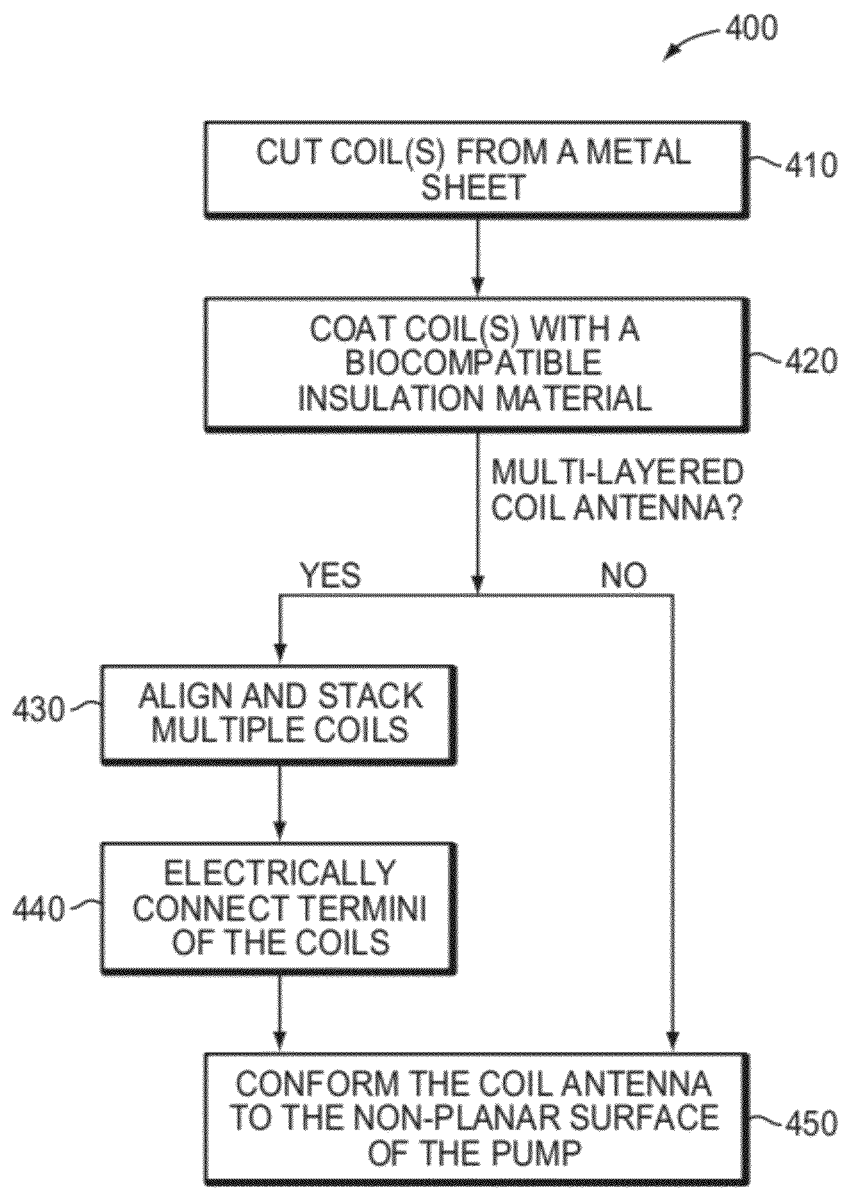
FIG. 4 is a flow chart illustrating a method for manufacturing the coil antenna in accordance with an embodiment of the invention.

A representative method 400 for manufacturing a coil antenna that conforms to a non-planar (e.g., dome-shaped) surface in accordance with embodiments of the current invention is shown in FIG. 4. In a first step 410, one or more spiral coils are cut from a sheet of metal (e.g., a 24K gold sheet having approximately 0.1 mm of thickness); the coil includes multiple windings of increasing diameter around a central point. The pattern of this spiral coil may be designed and programmed prior to cutting using suitable software (such as computer-aided design (CAD) software). In one embodiment, the metal sheet is attached to a flat glass plate, e.g., with water-soluble wax, to retain the flatness of the sheet during the cutting process. The cut coil can be released from the plate in warm water; appropriate chemical cleaning may be necessary to remove the wax residues and burrs of the coil. In a second, optional step 420, the coil is coated with a biocompatible insulation material, such as parylene. If a multi-layered coil antenna is preferred, multiple coils are first aligned and stacked on top of one another (step 430). In some embodiments, an adhesive, such as epoxy or silicone, is applied to multiple locations between two coils to ensure alignment of the coils and avoid vertical electrical contact therebetween; the adhesive is then cured in an oven at an appropriate temperature. Once the multiple coils and the associated inner termini are aligned, the termini are electrically connected, using, for example, resistance welding or laser welding, to form an antenna (step 440). In a step 450, the generated coil antenna is permanently conformed to the non-planar surface of the implantable pump. Each winding of the coils is spaced apart or insulated from other windings such that windings are not in lateral electrical contact, thereby functioning as an antenna.

In one embodiment, the coil antenna is conformed by placing the antenna into a shell that conforms to the non-planar surface (e.g., by inserting it into a slit, or placing it between two shell halves and then permanently attaching the shell halves to each other). In another embodiment, the coil antenna is conformed to the surface of a mold that is shaped to conform to the non-planar surface; an adhesive is then applied to the coil antenna to retain the surface mold shape. In one implementation, the coil antenna is first placed into a mold; a shell material is then injected into the mold around the coil(s) and cured in the oven at an appropriate temperature.

After curing, the shell material having the coil antenna embedded therein is released from the mold. In another implementation, the adhesive is sprayed onto the coil structure. The shell material may, but need not completely surround the coil windings.

Coil antennas manufactured utilizing the cutting approach described above can be individually characterized with similar parameters and advantageously conformed to various geometries of drug-delivery pumps implanted in different anatomical regions. Additionally, because the coils can be cut from metal sheets of any desired thickness, the amount of material from which the antenna is formed is not limited; this allows producing antennas that provide more power transfer than antennas made by traditional approaches, such as film deposition.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. For example, while coil antennas in accordance with the invention may be advantageously used in implantable drug pump devices, as described in detail above, they may also be integrated into other implantable devices and may, generally, be useful whenever antenna shapes conforming to non-planar surfaces are desired. Accordingly, the described embodiments are to be considered in all respects as only illustrative and not restrictive.

What is claimed is:

1. An implantable device for controllably ejecting fluid into an anatomic region, the device being shaped to conform to an anatomic implantation site and comprising:
    a fluid storage reservoir;
    a pump mechanism for pumping fluid from the reservoir into the anatomic region;
    circuitry for controlling the pump mechanism, the circuitry comprising a receiver for receiving wireless communications from an external transmitter and, operatively coupled to the receiver, an antenna comprising at least one spiral coil,
    wherein the device has a non-planar contour and the spiral coil comprises a plurality of windings of increasing diameter around a central point, the windings not being in lateral electrical contact with each other, and defines a non-planar surface conforming to the non-planar contour.

2. The device of claim 1, wherein each winding of the spiral comprises a conductive metal coated with a biocompatible insulating material.

3. The device of claim 2, wherein the biocompatible insulating material is parylene.

4. The device of claim 2, wherein each winding of the spiral is in contact with at least one adjacent winding.

5. The device of claim 1, wherein the non-planar contour is dome-shaped.

6. The device of claim 1, wherein the antenna is embedded into a shell of the implantable device.

7. The device of claim 1, wherein the device is a drug pump.

8. The device of claim 1, wherein the antenna comprises first and second coils each having a plurality of windings defining a spiral, the spiral of each coil itself defining a non-planar surface conforming to the non-planar contour, the second coil being aligned with and stacked on top of the first coil.

9. The device of claim 8, wherein an interior terminus of the first spiral coil winding is electrically connected to an interior terminus of the second spiral coil winding.

10. The device of claim 1, wherein the control circuitry is configured to wirelessly receive, via the antenna, at least one of power or data.

11. The device of claim 10, wherein the control circuitry is configured to wirelessly receive data by at least one of RF-coupled telemetry or inductively coupled telemetry.

12. The device of claim 1, wherein the spiral coil windings are laser-cut from a sheet of metal.

13. The device of claim 1, wherein the plurality of windings are concentric.

* * * * *